(12) United States Patent
Dollinger et al.

(10) Patent No.: US 8,530,384 B2
(45) Date of Patent: Sep. 10, 2013

(54) HERBICIDES BASED ON SUBSTITUTED THIEN-3-YL-SULPHONYLAMINO(THIO) CARBONYL-TRIAZOLIN(THI)ONES AND 4-HPPD-INHIBITORS

(75) Inventors: Markus Dollinger, Lyons (FR);
Hans-Joachim Santel, Leverkusen (DE); Ernst Rudolf Gesing, Erkrath (DE); Erwin Hacker, Hochheim (DE)

(73) Assignee: Bayer CropScience AG, Monheim (DE)

( * ) Notice: Subject to any disclaimer, the term of this patent is extended or adjusted under 35 U.S.C. 154(b) by 759 days.

(21) Appl. No.: 10/591,674

(22) PCT Filed: Feb. 19, 2005

(86) PCT No.: PCT/EP2005/001739
§ 371 (c)(1),
(2), (4) Date: Aug. 13, 2007

(87) PCT Pub. No.: WO2005/087004
PCT Pub. Date: Sep. 22, 2005

(65) Prior Publication Data
US 2008/0004180 A1 Jan. 3, 2008

(30) Foreign Application Priority Data
Mar. 5, 2004 (DE) .......................... 10 2004 010 813

(51) Int. Cl.
*A01N 25/00* (2006.01)
(52) U.S. Cl.
USPC ...................................................... 504/116.1
(58) Field of Classification Search
USPC .............................................. 504/103, 116.1
See application file for complete search history.

(56) References Cited

U.S. PATENT DOCUMENTS

| | | | |
|---|---|---|---|
| 6,162,762 A | 12/2000 | Cornes et al. | |
| 6,200,931 B1 | 3/2001 | Müller et al. | |
| 6,649,565 B1 | 11/2003 | Feucht et al. | |
| 6,964,939 B1 | 11/2005 | Gesing et al. | |
| 2003/0078167 A1* | 4/2003 | Ziemer et al. | 504/271 |
| 2005/0003963 A1* | 1/2005 | Feucht et al. | 504/139 |
| 2008/0020932 A1 | 1/2008 | Dollinger et al. | |

FOREIGN PATENT DOCUMENTS

| | | |
|---|---|---|
| WO | WO 01/05788 A1 | 1/2001 |
| WO | WO 01/15533 A1 | 3/2001 |
| WO | WO 03/026426 A1 | 4/2003 |

OTHER PUBLICATIONS

Dialog File 351, Accession No. 13813255, Derwent WPI English language abstract for WO 03/026426 A1.
Office Action mailed Feb. 7, 2008, in U.S. Appl. No. 10/591,673, Dollinger, et al., filed Jun. 13, 2007.
Office Action mailed Nov. 14, 2008, in U.S. Appl. No. 10/591,673, Dollinger, et al., filed Jun. 13, 2007.
Office Action mailed Jun. 24, 2009, in U.S. Appl. No. 10/591,673, Dollinger, et al., filed Jun. 13, 2007.
Office Action mailed Mar. 21, 2006, in U.S. Appl. No. 10/489,086, Feucht, et al., filed Aug. 12, 2004.
Office Action mailed Dec. 22, 2006, in U.S. Appl. No. 10/489,086, Feucht, et al., filed Aug. 12, 2004.
Office Action mailed Sep. 18, 2007, in U.S. Appl. No. 10/489,086, Feucht, et al., filed Aug. 12, 2004.
Office Action mailed Feb. 5, 2008, in U.S. Appl. No. 10/489,086, Feucht, et al., filed Aug. 12, 2004.
Office Action mailed Oct. 28, 2008, in U.S. Appl. No. 10/489,086, Feucht, et al., filed Aug. 12, 2004.
Office Action mailed Jun. 5, 2009, in U.S. Appl. No. 10/489,086, Feucht, et al., filed Aug. 12, 2004.
Bauer, T.A., et al., "Response of Selected Weed Species to Postemergence Imazethapyr and Bentazon," *Weed Tech.* 9:236-242, The Weed Science Society of America (1995).
Blackshaw, R.E., et al., "Herbicide Combinations for Postemergent Weed Control in Safflower (*Carthamus tinctorius*)," *Weed Tech.* 4:97-104, The Weed Science Society of America (1990).
Blackshaw, R.E., "HOE-39866 Use in Chemical Fallow Systems," *Weed Tech.* 3:420-428, The Weed Science Society of America (1989).
Blackshaw, R.E., "Synergistic Mixes of DPX-A7881 and Clopyralid in Canola (*Brassica napus*)," *Weed Tech.* 3:690-695, The Weed Science Society of America (1989).

(Continued)

*Primary Examiner* — Fereydoun G Sajjadi
*Assistant Examiner* — Danielle Sullivan
(74) *Attorney, Agent, or Firm* — Sterne, Kessler, Goldstein & Fox P.L.L.C.

(57) ABSTRACT

The invention relates to herbicidal compositions comprising an effective amount of an active ingredient combination composed of
(a) at least one substituted thien-3-ylsulfonylamino(thio) carbonyltriazolin(thi)one of the formula (I)

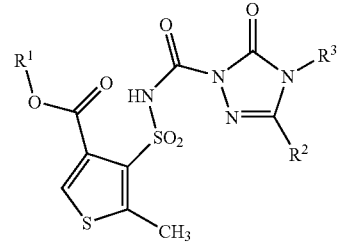

in which
$R^1$, $R^2$ and $R^3$ are as defined in the description,
— or salts of the compounds of the formula (I)—
and
(b) one or more compounds from a second group of herbicides which comprises selected 4-HPPD inhibitors,
and, if desired, additionally
(c) a crop plant tolerance promoter compound.
The invention further relates to the use of the compositions for controlling unwanted plant growth and to a process for producing the compositions.

5 Claims, No Drawings

(56) References Cited

OTHER PUBLICATIONS

Blouin, D.C., et al., "Analysis of Synergistic and Antagonistic Effects of Herbicides Using Nonlinear Mixed-Model Methodology," *Weed Tech. 18*:464-472, The Weed Science Society of America (2004).

Bradley, P.R., et al., "Response of Sorghum (*Sorghum bicolor*) to Atrazine, Ammonium Sulfate, and Glyphosate," *Weed Tech. 14*:15-18, The Weed Science Society of America (2000).

Buker, III, R.S., et al., "Confirmation and Control of a Paraquat-Tolerant Goosegrass (*Eleusine indica*) Biotype," *Weed Tech. 16*:309-313, The Weed Science Society of America (2002).

Burke, I.C., et al., "CGA-362622 Antagonizes Annual Grass Control with Clethodim," *Weed Tech. 16*:749-754, The Weed Science Society of America (2002).

Flint, J.L., et al., "Analyzing Herbicide Interactions, A Statistical Treatment of Colby's Method," *Weed Tech. 2*:304-309, The Weed Science Society of America (1988).

Gillespie, G.R., and Nalewaja, J.D., "Wheat (*Triticum aestivum*) Response to Triallate Plus Chlorsulfuron," *Weed Tech. 3*:20-23, The Weed Science Society of America (1989).

Green, J.M., et al., "Metribuzin and Chlorimuron Mixtures for Preemergence Broadleaf Weed Control in Soybeans, *Glycine max*," *Weed Tech. 2*:355-363, The Weed Science Society of America (1988).

Harker, N.K., and O'Sullivan, P.A., "Synergistic Mixtures of Sethoxydim and Fluazifop on Annual Grass Weeds," *Weed Tech. 5*:310-316, The Weed Science Society of America (1991).

Kent, L.M., et al., "Effect of Ammonium Sulfate, Imazapyr, and Environment on the Phytotoxicity of Imazethapyr," *Weed Tech. 5*:202-205, The Weed Science Society of America (1991).

Kotoula-Syka, E., et al., "Interactions between SAN 582H and Selected Safeners on Grain Sorghum (*Sorghum bicolor*) and Corn (*Zea mays*)," *Weed Tech. 10*:299-304, The Weed Science Society of America (1996).

Lanclos, D.Y., et al., "Glufosinate Tank-Mix Combinations in Glufosinate-Resistant Rice (*Oryza sativa*)," *Weed Tech. 16*:659-663, The Weed Science Society of America (2002).

Norris, J.L., et al., "Weed Control from Herbicide Combinations with Three Formulations of Glyphosate," *Weed Tech. 15*:552-558, The Weed Science Society of America (2001).

Novosel, K.M., et al., "Metolachlor Efficacy as Influenced by Three Acetolactate Synthase-Inhibiting Herbicides," *Weed Tech. 12*:248-253, The Weed Science Society of America (1998).

Palmer, E.W., et al., "Broadleaf Weed Control in Soybean (*Glycine max*) with CGA-277476 and Four Postemergence Herbicides," *Weed Tech. 14*:617-623, The Weed Science Society of America (2000).

Salzman, F.P., and Renner, K.A., "Response of Soybean Combinations of Clomazone, Metribuzin, Linuron, Alachlor, and Atrazine," *Weed Tech. 6*:922-929, The Weed Science Society of America (1992).

Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech. 12*:463-469, The Weed Science Society of America (1998).

Shaw, D.R. and Arnold, J.C., "Weed Control from Herbicide Combinations with Glyphosate," *Weed Tech. 16*:1-6, The Weed Science Society of America (2002).

Snipes, C.E., and Allen, R.L., "Interaction of Graminicides Applied in Combination with Pyrithiobac," *Weed Tech. 10*:889-892, The Weed Science Society of America (1996).

Wehtje, G. and Walker, R.H., "Interaction of Glyphosate and 2,4-DB for the Control of Selected Morningglory (*Ipomoea* spp.) Species," *Weed Tech. 11*:152-156, The Weed Science Society of America (1997).

Zhang, W., et al., "Fenoxaprop Interactions for Barnyardgrass (*Echinochloa crus-galli*) Control in Rice," *Weed Tech. 19*:293-297, The Weed Science Society of America (2005).

Rummens, F.H.A., "An Improved Definition of Synergistic and Antagonistic Effects," Weed Science 23:4-6 (1975).

Notice of Allowance mailed Jul. 2, 2010, in U.S. Appl. No. 10/489,086, Feucht, et al., filed Aug. 12, 2004.

\* cited by examiner

HERBICIDES BASED ON SUBSTITUTED THIEN-3-YL-SULPHONYLAMINO(THIO) CARBONYL-TRIAZOLIN(THI)ONES AND 4-HPPD-INHIBITORS

The invention relates to novel herbicidal synergistic active ingredient combinations which comprise known substituted thien-3-ylsulfonylamino(thio)carbonyltriazolin(thi)ones on the one hand and one or more known herbicidal compounds on the other hand and, if desired, additionally a crop plant tolerance promoter compound and can be used with particular success for weed control in various crops of useful plants or else for controlling monocotyledonous and dicotyledonous weeds in the semiselective and nonselective segment.

Substituted thien-3-ylsulfonylamino(thio)carbonyltriazolin(thi)ones are known to be effective herbicides (cf. WO-A-01/05788). Additionally, herbicides comprising these compounds and other known herbicides or safeners are known (cf. WO-A-03/026427 and WO-A-03/026426). The action of these herbicides, however, is not entirely satisfactory under all conditions.

Surprisingly it has now been found that a series of active ingredients from the class of the substituted thien-3-ylsulfonylamino(thio)carbonyltriazolin(thi)ones, when applied jointly with certain herbicidal compounds, display synergistic effects in terms of their action against weeds, and can be used with particular advantage as broad-spectrum combination products for selectively controlling monocotyledonous and dicotyledonous weeds in crops of useful plants, such as in cotton, barley, potatoes, corn, oilseed rape, rice, rye, soya, sunflowers, wheat, sugarcane and sugarbeet, but also for controlling monocotyledonous and dicotyledonous weeds in the semiselective and nonselective segment.

The invention provides herbicidal compositions comprising an effective amount of an active ingredient combination composed of
(a) at least one substituted thien-3-ylsulfonylamino(thio) carbonyltriazolin(thi)one of the formula (I)

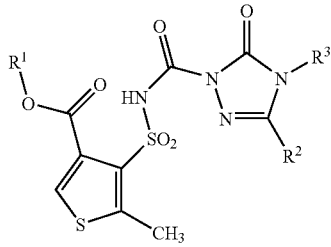

(I)

in which
$R^1$ is optionally cyano-, halogen- or $C_1$-$C_4$-alkoxy-substituted alkyl having 1 to 6 carbon atoms,
$R^2$ is hydrogen, hydroxyl, mercapto, amino, cyano, fluorine, chlorine, bromine or iodine, is optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, is in each case optionally fluorine-, chlorine- and/or bromine-substituted alkenyl or alkynyl having in each case 2 to 6 carbon atoms, is in each case optionally fluorine-, chlorine-, cyano-, $C_1$-$C_4$-alkoxy- or $C_1$-$C_4$-alkoxy-carbonyl-substituted alkoxy, alkylthio, alkylamino or alkylcarbonylamino having in each case 1 to 6 carbon atoms in the alkyl group, is alkenyloxy, alkynyloxy, alkenylthio, alkynylthio, alkenylamino or alkynylamino having in each case 3 to 6 carbon atoms in the alkenyl or alkynyl group, is dialkylamino having in each case 1 to 4 carbon atoms in the alkyl groups, is in each case optionally methyl- and/or ethyl-substituted aziridino, pyrrolidino, piperidino or morpholino, is in each case optionally fluorine-, chlorine-, bromine-, cyano- and/or $C_1$-$C_4$-alkyl-substituted cycloalkyl, cycloalkenyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl or cycloalkenyl group and optionally 1 to 4 carbon atoms in the alkyl moiety, or is in each case optionally fluorine-, chlorine-, bromine-, cyano-, nitro-, $C_1$-$C_4$-alkyl-, trifluoromethyl-, $C_1$-$C_4$-alkoxy- and/or $C_1$-$C_4$-alkoxy-carbonyl-substituted aryl, arylalkyl, aryloxy, arylalkoxy, arylthio, arylalkylthio, arylamino or arylalkylamino having in each case 6 or 10 carbon atoms in the aryl group and optionally 1 to 4 carbon atoms in the alkyl moiety, $R^3$ is hydrogen, hydroxyl, amino, cyano, is $C_2$-$C_{10}$-alkylideneamino, is optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, is in each case optionally fluorine-, chlorine- and/or bromine-substituted alkenyl or alkynyl having in each case 2 to 6 carbon atoms, is in each case optionally fluorine-, chlorine-, bromine-, cyano-, $C_1$-$C_4$-alkoxy- or $C_1$-$C_4$-alkoxy-carbonyl-substituted alkoxy, alkylamino or alkyl-carbonylamino having in each case 1 to 6 carbon atoms in the alkyl group, is alkenyloxy having 3 to 6 carbon atoms, is dialkylamino having in each case 1 to 4 carbon atoms in the alkyl groups, is in each case optionally fluorine-, chlorine-, bromine-, cyano- and/or $C_1$-$C_4$-alkyl-substituted cycloalkyl, cycloalkylamino or cycloalkylalkyl having in each case 3 to 6 carbon atoms in the alkyl group and optionally 1 to 4 carbon atoms in the alkyl moiety, or is in each case optionally fluorine-, chlorine-, bromine-, cyano-, nitro-, $C_1$-$C_4$-alkyl-, trifluoromethyl- and/or $C_1$-$C_4$-alkoxy-substituted aryl or arylalkyl having in each case 6 or 10 carbon atoms in the aryl group and optionally 1 to 4 carbon atoms in the alkyl moiety —or salts of the compounds of the formula (I)—

("active ingredients of group 1")

and (b) one or more compounds from a second group of herbicides which includes the following active ingredients:

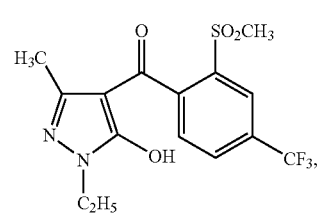

Compound B.1

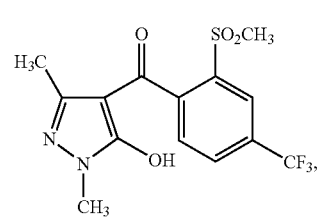

Compound B.2

Compound B.3
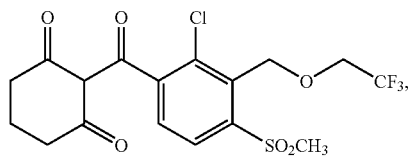

Compound B.4
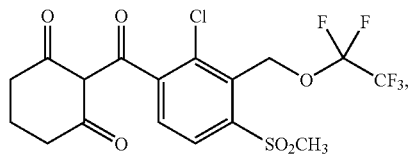

Compound B.5
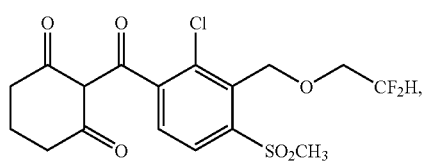

Compound B.6
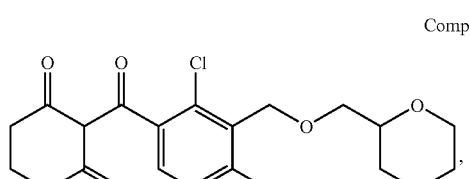

Compound B.7
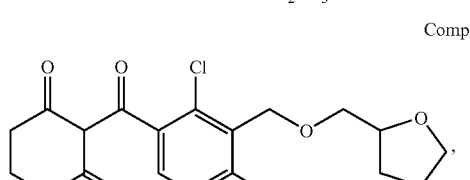

Compound B.8
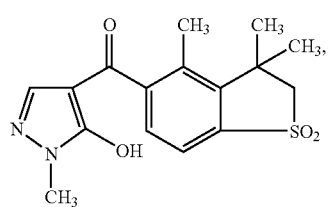

Compound B.9
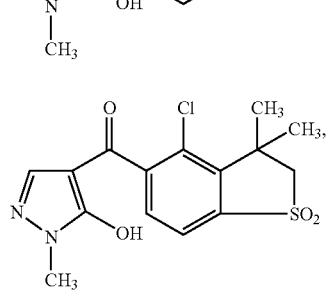

Compound B.10
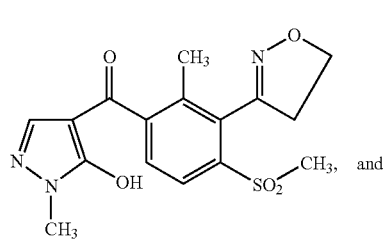

Compound B.11
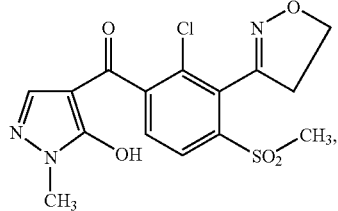

("active ingredients of group 2"),
and, if desired, additionally (c) a crop plant tolerance promoter compound from the following group of compounds:
4-dichloroacetyl-1-oxa-4-azaspiro[4.5]decane (AD-67), 4-dichloroacetyl-3,4-dihydro-3-methyl-2H-1,4-benzoxazine (benoxacor), 5-chloroquinoxalin-8-oxyacetic acid 1-methylhexyl ester (cloquintocet-mexyl), 2,4-dichlorophenoxyacetic acid (2,4-D), 2,2-dichloro-N,N-di-2-propenylacetamide (dichlormid), N-(4-methylphenyl)-N'-(1-methyl-1-phenylethyl) urea (daimuron), 4,6-dichloro-2-phenylpyrimidine (fenclorim), 1-(2,4-dichlorophenyl)-5-trichloromethyl-1H-1,2,4-triazole-3-carboxylic acid ethyl ester (fenchlorazole-ethyl), 2-chloro-4-trifluoromethylthiazole-5-carboxylic acid phenylmethyl ester (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole), ethyl 4,5-dihydro-5,5-diphenyl-3-isoxazolecarboxylate (isoxadifen-ethyl), (4-chloro-2-methylphenoxy)acetic acid (MCPA), (±)-2-(4-chloro-2-methylphenoxy)propanoic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191, CAS Reg. No. 96420-72-3), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl) acetamide (PPG-1292), 3-dichloroacetyl-2,2,5-trimethyloxazolidine (R-29148), N-cyclopropyl-4-[[(2-methoxy-5-methylbenzoyl)amino]-sulfonyl] benzamide, N-[[(4-methylaminocarbonylamino) phenyl]-sulfonyl-2-methoxybenzamide (known from WO-A-99/66795), and compounds of the acylsulfamoylbenzoamide type, of formula (II) below for example, which are known for example from WO 99/16744, (II)
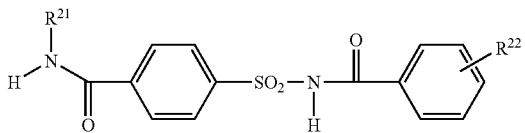

| Compound No. | $R^{21}$ | $R^{22}$ |
|---|---|---|
| S 3-1 | cyclopropyl | 2-OCH$_3$ |
| S 3-2 | cyclopropyl | 2-OCH$_3$, 5-Cl |
| S 3-3 | ethyl | 2-OCH$_3$ |
| S 3-4 | isopropyl | 2-OCH$_3$, 5-Cl |
| S 3-5 | isopropyl | 2-OCH$_3$ |

("active ingredients of group 3").

Examples of the compounds of the formula (I) which are preferred as active ingredient components of the invention are listed in Table 1 below.

| Ex. No. | $R^1$ | $R^2$ | $R^3$ | Melting point (° C.) |
|---|---|---|---|---|
| I-1 | $CH_3$ | $OC_2H_5$ | $CH_3$ | 163 |
| I-2 | $CH_3$ | $OCH_3$ | $CH_3$ | 201 |
| I-3 | $CH_3$ | $OCH_3$ |  | 218 |
| I-4 | $CH_3$ | $OC_3H_7$-n |  | 156 |

The active ingredients of group 2 are known active herbicidal ingredients. Thus the compounds B.1 to B.2 are known from WO 01/74785, the active ingredients B.3 to B.7 from WO 00/21924, and the other active ingredients from WO 96/26206, WO 96/25412, and US 20020016262.

All active ingredients of group 2 are what are known as 4-HPPD inhibitors, which all show similar synergism effects in combination with the compounds of the formula (I).

The compositions of the invention preferably contain one or two active ingredients of group 1, one to three active ingredients of group 2, and, if desired, one active ingredient of group 3.

In particular the compositions of the invention contain one active ingredient of group 1, one or two active ingredients of group 2, and, if desired, one active ingredient of group 3.

Preference among the compounds of the formula (I) is given to the compound I-2 and its salts, especially the sodium salt. The most preferred is the compound I-2.

The compounds of group 3 are likewise known compounds, which are known for example from Pesticide Manual, 13$^{th}$ edition, editor: C. D. S. Tomlin, 2003.

Preferred among the active ingredients of group 3 are benoxacor, mefenpyr, fenchlorazole, isoxadifen, cloquintocet, and their $C_1$-$C_{10}$-alkyl esters, especially benoxacor (S 4-1), mefenpyr-diethyl (S 1-1), fenchlorazol-ethyl (S 1-6), isoxadifen-ethyl (S 1-9), cloquintocet-mexyl (S 2-1), and the compound (S 3-1).

The following two-way active ingredient combinations of the invention may be mentioned on account of their particularly advantageous weed control properties, especially in corn crops and cereal crops:

I-1+B.1, I-1+B.2, I-1+B.3, I-1+B.4, I-1+B.5, I-1+B.6, I-1+B.7, I-1+B.8, I-1+B.9, I-1+B.10, I-1+B.11, I-2+B.1, I-2+B.2, I-2+B.3, I-2+B.4, I-2+B.5, I-2+B.6, I-2+B.7, I-2+B.8, I-2+B.9, I-2+B.10, I-2+B.11, I-3+B.1, I-3+B.2, I-3+B.3, I-3+B.4, I-3+B.5, I-3+B.6, I-3+B.7, I-3+B.8, I-3+B.9, I-3+B.10, I-3+B.11, I-4+B.1, I-4+B.2, I-4+B.3, I-4+B.4, I-4+B.5, I-4+B.6, I-4+B.7, I-4+B.8, I-9, I-4+B.10, I-4+B.11.

The most preferred are the following two-way combinations with the preferred active ingredients of group 3

I-1+B.1+S 4-1, I-1+B.2+S 4-1, I-1+B.3+S 4-1, I-1+B.4+S 4-1, I-1+B.5+S 4-1, I-1+B.6+S 4-1, I-1+B.7+S 4-1, I-1+B.8+S 4-1, I-1+B.9+S 4-1, I-1+B.10+S 4-1, I-1+B.11+S 4-1, I-2+B.1+S 4-1, I-2+B.2+S 4-1, I-2+B.3+S 4-1, I-2+B.4+S 4-1, I-2+B.5+S 4-1, I-2+B.6+S 4-1, I-2+B.7+S 4-1, I-2+B.8+S 4-1, I-2+B.9+S 4-1, I-2+B.10+S 4-1, I-2+B.11+S 4-1, I-3+B.1+S 4-1, I-3+B.2+S 4-1, I-3+B.3+S 4-1, I-3+B.4+S 4-1, I-3+B.5+S 4-1, I-3+B.6+S 4-1, I-3+B.7+S 4-1, I-3+B.8+S 4-1, I-3+B.9+S 4-1, I-3+B.10+S 4-1, I-3+B.11+S 4-1, I-4+B.1+S 4-1, I-4+B.2+S 4-1, I-4+B.3+S 4-1, I-4+B.4+S 4-1, I-4+B.5+S 4-1, I-4+B.6+S 4-1, I-4+B.7+S 4-1, I-4+B.8+S 4-1, I-4+B.9+S 4-1, I-4+B.10+S 4-1, I-4+B.11+S 4-1 and I-1+B.1+S 1-1, I-1+B.2+S 1-1, I-1+B.3+S 1-1, I-1+B-4+S 1-1, I-1+B.5+S 1-1, I-1+B.6+S 1-1, I-1+B.7+S 1-1, I-1+B.8+S 1-1, I-1+B.9+S 1-1, I-1+B.10+S 1-1, I-1+B.11+S 1-1, I-2+B.1+S 1-1, I-2+B.2+S 1-1, I-2+B.3+S 1-1, I-2+B.4+S 1-1, I-2+B.5+S 1-1, I-2+B.6+S 1-1, I-2+B.7+S 1-1, I-2+B.8+S 1-1, I-2+B.9+S 1-1, I-2+B.10+S 1-1, I-2+B.11+S 1-1, I-3+B.1+S 1-1, I-3+B.2+S 1-1, I-3+B.3+S 1-1, I-3+B.4+S 1-1, I-3+B.5+S 1-1, I-3+B.6+S 1-1, I-3+B.7+S 1-1, I-3+B.8+S 1-1, I-3+B.9+S 1-1, I-3+B.10+S 1-1, I-3+B.11+S 1-1, I-4+B.1+S 1-1, I-4+B.2+S 1-1, I-4+B.3+S 1-1, I-4+B.4+S 1-1, I-4+B.5+S 1-1, I-4+B.6+S 1-1, I-4+B.7+S 1-1, I-4+B.8+S 1-1, I-4+B.9+S 1-1, I-4+B.10+S 1-1, I-4+B.11+S 1-1 and I-1+B.1+S 1-6, I-1+B.2+S 1-6, I-1+B.3+S 1-6, I-1+B.4+S 1-6, I-1+B.5+S 1-6, I-1+B.6+S 1-6, I-1+B.7+S 1-6, I-1+B.8+S 1-6, I-1+B.9+S 1-6, I-1+B.10+S 1-6, I-1+B.11+S 1-6, I-2+B.1+S 1-6, I-2+B.2+S 1-6, I-2+B.3+S 1-6, I-2+B.4+S 1-6, I-2+B.5+S 1-6, I-2+B.6+S 1-6, I-2+B.7+S 1-6, I-2+B.8+S 1-6, I-2+B.9+S 1-6, I-2+B.10+S 1-6, I-2+B.11+S 1-6, I-3+B.1+S 1-6, I-3+B.2+S 1-6, I-3+B.3+S 1-6, I-3+B.4+S 1-6, I-3+B.5+S 1-6, I-3+B.6+S 1-6, I-3+B.7+S 1-6, I-3+B.8+S 1-6, I-3+B.9+S 1-6, I-3+B.10+S 1-6, I-3+B.11+S 1-6, I-4+B.1+S 1-6, I-4+B.2+S 1-6, I-4+B.3+S 1-6, I-4+B.4+S 1-6, I-4+B.5+S 1-6, I-4+B.6+S 1-6, I-4+B.7+S 1-6, I-4+B.8+S 1-6, I-4+B.9+S 1-6, I-4+B.10+S 1-6, I-4+B.11+S 1-6 and I-1+B.1+S 1-9, I-1+B.2+S 1-9, I-1+B.3+S 1-9, I-1+B.4+S 1-9, I-1+B.5+S 1-9, I-1+B.6+S 1-9, I-1+B.7+S 1-9, I-1+B.8+S 1-9, I-1+B.9+S 1-9, I-1+B.10+S 1-9, I-1+B.11+S 1-9, I-2+B.1+S 1-9, I-2+B.2+S 1-9, I-2+B.3+S 1-9, I-2+B.4+S 1-9, I-2+B.5+S 1-9, I-2+B.6+S 1-9, I-2+B.7+S 1-9, I-2+B.8+S 1-9, I-2+B.9+S 1-9, I-2+B.10+S 1-9, I-2+B.11+S 1-9, I-3+B.1+S 1-9, I-3+B.2+S 1-9, I-3+B.3+S 1-9, I-3+B.4+S 1-9, I-3+B.5+S 1-9, I-3+B.6+S 1-9, I-3+B.7+S 1-9, I-3+B.8+S 1-9, I-3+B.9+S 1-9, I-3+B.10+S 1-9, I-3+B.11+S 1-9, I-4+B.1+S 1-9, I-4+B.2+S 1-9, I-4+B.3+S 1-9, I-4+B.4+S 1-9, I-4+B.5+S 1-9, I-4+B.6+S 1-9, I-4+B.7+S 1-9, I-4+B.8+S 1-9, I-4+B.9+S 1-9, I-4+B.10+S 1-9, I-4+B.11+S 1-9 and I-1+B.1+S 2-1, I-1+B.2+S 2-1, I-1+B.3+S 2-1, I-1+B.4+S 2-1, I-1+B.5+S 2-1, I-1+B.6+S 2-1, I-1+B.7+S 2-1, I-1+B.8+S 2-1, I-1+B.9+S 2-1, I-1+B.10+S 2-1, I-1+B.11+S 2-1, I-2+B.1+S 2-1, I-2+B.2+S 2-1, I-2+B.3+S 2-1, I-2+B.4+S 2-1, I-2+B.5+S 2-1, I-2+B.6+S 2-1, I-2+B.7+S 2-1, I-2+B.8+S 2-1, I-2+B.9+S 2-1, I-2+B.10+S 2-1, I-2+B.11+S 2-1, I-3+B.1+S 2-1, I-3+B.2+S 2-1, I-3+B.3+S 2-1, I-3+B.4+S 2-1, I-3+B.5+S 2-1, I-3+B.6+S 2-1, I-3+B.7+S 2-1, I-3+B.8+S 2-1, I-3+B.9+S 2-1, I-3+B.10+S 2-1, I-3+B.11+S 2-1, I-4+B.1+S 2-1, I-4+B.2+S 2-1, I-4+B.3+S 2-1, I-4+B.4+S 2-1, I-4+B.5+S 2-1, I-4+B.6+S 2-1, I-4+B.7+S 2-1, I-4+B.8+S 2-1, I-4+B.9+S 2-1, I-4+B.10+S 2-1, I-4+B.11+S 2-1 and I-1+B.1+S 3-1, I-1+B.2+S 3-1, I-1+B.3+S 3-1, I-1+B.4+S 3-1, I-1+B.5+S 3-1, I-1+B.6+S 3-1, I-1+B.7+S 3-1, I-1+B.8+S 3-1, I-1+B.9+S 3-1, I-1+B.10+S 3-1, I-1+B.11+S 3-1, I-2+B.1+S 3-1, I-2+B.2+S 3-1, I-2+B.3+S 3-1, I-2+B.4+S 3-1, I-2+B.5+S 3-1, I-2+B.6+S 3-1, I-2+B.7+S 3-1, I-2+B.8+S 3-1, I-2+B.9+S 3-1, I-2+B.10+S 3-1, I-2+B.11+S 3-1, I-3+B.1+S 3-1, I-3+B.2+S 3-1, I-3+B.3+S 3-1, I-3+B.4+S 3-1, I-3+B.5+S 3-1, I-3+B.6+S 3-1, I-3+B.7+S 3-1, I-3+B.8+S 3-1, I-3+B.9+S 3-1, I-3+B.10+S 3-1, I-3+B.11+S 3-1, I-4+B.1+S 3-1, I-4+B.2+S 3-1, I-4+B.3+S 3-1, I-4+B.4+S 3-1, I-4+B.5+S 3-1, I-4+B.6+S 3-1, I-4+B.7+S 3-1, I-4+B.8+S 3-1, I-4+B.9+S 3-1, I-4+B.10+S 3-1, I-4+B.11+S 3-1.

In all of the active ingredient combinations listed explicitly above, with and without addition of safener, the compounds of the formula (I) can also be replaced by their salts, particularly their sodium salt.

These mixtures, moreover, have additional advantages in some cases, these advantages being manifested in improved properties on the part of the active ingredient formulation, such as activity or storage stability, for example.

All of the active ingredient combinations listed individually may if appropriate, in order to improve the active properties with respect to weeds and/or to improve the selectivity with respect to the crop plants, may be admixed with one of the following herbicides, which are known from the e-Pesticide Manual of the British Crop Protection Council, 2002-2003, 12$^{th}$ edition, Editor C. D. S. Tomlin, from WO 03/026426, or from the references cited:

acetochlor (C.1), acifluorfen, acifluorfen-sodium (C.2), aclonifen (C.3), alachlor (C.4), alloxydim (C.5), alloxydim-sodium, (C.6), ametryn (C.7), amicarbazone (C.8), amidosulfuron (C.9), amitrole (C.10), anilofos (C.11), asulam (C.12), and asulam-sodium (C.13), atrazine (C.14), azafenidin (C.15), azimsulfuron (C.16), beflubutamid (C.17), benazolin (C.18), and benazolin-ethyl (C.19), benfluralin (C.20), benfuresate (C.21), bensulfuron-methyl (C.22), bentazone (C.23), benthiocarb (C.24), benzfendizone (C.25), benzobicyclon (C.26), benzofenap (C.274), bifenox (C.275), bispyribac-sodium (C.27), bromacil (C.28), bromobutide (C.29), bromofenoxim (C.30), bromoxynil (C.31), bromoxynil-heptanoate (C.32), bromoxynil-octanoate (C.33), bromoxynil-potassium (C.34), butachlor (C.35), butafenacil (C.36), butralin (C.37), butroxydim (C.38), butylate (C.39), cafenstrole (C.40), carbetamide (C.41), carfentrazone-ethyl (C.42), chlometoxyfen (C.43), chloridazon (C.44), chlorimuron-ethyl (C.45), chlornitrofen (C.46), chlorotoluron (C.47), chlorsulfuron (C.48), cinidon-ethyl (C.50), cinmethylin (C.51), cinosulfuron (C.52), clefoxydim (C.53), clethodym (C.54), clodinafop-propargyl (C.55), clomazone (C.56), clomeprop (C.57), clopyralid (C.58), cloransulam-methyl (C.59), cumyluron (C.60), cyanazine (C.61), cyclosulfamuron (C. 62), cycloxydim (C.63), cyhalofop-butyl (C.64), 2,4-D (C.65) and its salts (C.66), amines (C.67), and esters (C.68), desmedipham (C.69), dicamba (C.70) and its salts (C.71), dicamba-diolamine (C.72), dichlobenil (C.73), dichlorprop-P (C.74), diclofop-methyl (C.75), diclosulam (C.76), difenzoquat (C.77), difenzoquat metilsulfate (C.78), diflufenican (C.79), diflufenzopyr (C.80), dimefuron (C.81), dimepiperate (C.82), dimethachlor (C.83), dimethametryn (C.84), dimethenamid (C.85), dimthenamid-P (C.86), dimexyflam (C.87), diquat-dibromide (C.88), dithiopyr (C.89), diuron (C.90), dymron (C.91), EPTC (C.92), esprocarb (C.93), ethalfluralin (C.94), ethametsulfuron-methyl (C.95), ethofumesate (C.96), ethoxyfen (C.97), ethoxysulfuron (C.98) and its sodium salt (C.99), ethobenzanid (C.100), fenoxaprop-P-ethyl (C.101), fentrazamide (C.102), flamprop-M-methyl (C.103) and -M-isopropyl (C.104), flazasulfuron (C.105), florasulam (C.106), fluazifop-P-ethyl (C.107), fluazifop-P-butyl (C.108), flucarbazone-sodium (C.109), fluazolate (C.110), flufenacet (C.111), flufenpyr (C.112), flumetsulam (C.113), flumiclorac-pentyl (C.114), flumioxazin (C.115), flumipropyn (C.116), fluometuron (C.117), fluorochloridone (C.118), fuoroglycofen-ethyl (C.119), flupoxam (C.120), flupropacil (C.121), flupyrsulfuron-methyl (C.122) and its sodium salt (C.123), flurenol (C.124), fluroxypyr (C.125) and its esters (C.126) such as fluroxypyr-meptyl (C.127), flurtamone (C.128), fluthiacet-methyl (C.129), fomesafen (C.130), foramsulfuron (C.131), glufosinate (C.132), glufosinate-ammonium (C.133), glyphosate (C.134), glyphosate-ammonium (C.135), glyphosate-isopropylammonium (C.136), glyphosate-sodium (C.137), glyphosate-trimesium (C.138), halosulfuron-methyl (C.139), haloxyfop (C.140), -methyl (C.141), -P-methyl (C.142), -ethoxyethyl (C.143) or -butyl (C.144), hexazinone (C.145), imazamethabenz-methyl (C.146), imazamox (C.147), imazapic (C.148), imazapyr (C.149), imazaquin (C.150), imazethapyr (C.151), imazosulfuron (C.152), indanofan (C.153), iodosulfuron-methyl-sodium (C.154), ioxynil (C.155), ioxynil-octanoate (C.156), ioxynil-sodium (C.157), isoproturon (C.158), isouron (C.159), isoxaben (C.160), isoxachlortole (C.161) ([4-chloro-2-(methylsulfonyl)phenyl](5-cyclopropyl-4-isoxazolyl)-methanone, known from EP 470 856), isoxaflutole (C.162), ketospiradox (C.163), lactofen (C.164), lenacil (C.165), linuron (C.166), MCPA (C.167), mecoprop-P (C.168), mefenacet (C.169), mesosulfuron-methyl (C.170) and its sodium salt (C.171), mesotrione (C.172), metamitron (C.173), metazachlor (C.174), methabenzthiazuron (C.175), metobromuron (C.176), metolachlor (C.177), S-metolachlor (C.178), metosulam (C.179), metoxuron (C.180), metribuzin (C.181), metsulfuron (C.182), metsulfuron-methyl (C.183), molinate (C.184), naproanilide (C.185), napropamide (C.186), neburon (C.187), nicosulfuron (C.188), norflurazon (C.189), orbencarb (C.190), oryzalin (C.191), oxadiargyl (C.192), oxadiazon (C.193), oxasulfuron (C.194), oxaziclomefone (C.195), oxyfluorfen (C.196), paraquat (C.197), pendimethalin (C.198), pendralin (C.199), penoxsulam (C.200), pentoxazone (C.201), penthoxamid (C.202), phenmedipham (C.203), picloram (C.204), picolinafen (C.205), piperophos (C.206), pretilachlor (C.207), primisulfuron-methyl (C. 208), profluazol (C.209), profoxydim (C.210), prometryn (C.211), propachlor (C.212), propanil (C.213), propaquizafop (C.49), propisochlor (C.214), propoxycarbazone-sodium (C.215), propyzamide (C.216), prosulfocarb (C.217), prosulfuron (C.218), pyraclonil (C.219) (1-(3-chloro-4,5,6,7-tetrahydropyrazolo[1,5-a]pyridin-2-yl)-5-(methyl-2-propynylamino)-1H-pyrazole-4-carbonitrile, known from WO 94/08999), pyraflufen-ethyl (C.220), pyrazolate (C.221), pyrazosulfuron-ethyl (C.222), pyrazoxyfen (C.223), pyribenzoxym (C.224), pyributicarb (C.225), pyridafol (C.226), pyridate (C.227), pyridatol (C. 228), pyriftalid (C. 229), pyriminobac-methyl (C.230), pyrithiobac-sodium (C.231), quinchlorac (C. 232), quinmerac (C.233), quinoclamine (C.234), quizalofop (C.235), -ethyl (C.236), -P-ethyl (C.237) and -P-tefuryl (C.238), rimsulfuron (C.239), sethoxydim (C.240), simazine (C.241), sulcotrione (C.242), sulfentrazone (C.243), sulfometuron-methyl (C.244), sulfosate (C.245), sulfosulfuron (C.246), tebuthiuron (C.247), tepraloxydim (C.248), terbuthylazine (C.249), terbutryn (C.250), thenylchlor (C.251), thiazopyr (C.252), thifensulfuron-methyl (C.253), thiocarbazil (C.254), tralkoxydim (C.255), triallate (C.256), triasulfuron (C.276), tribenuron-methyl (C.257), triclopyr (C.258), tridiphane (C.259), trifloxysulfuron (C.260), trifluralin (C.261), triflusulfuron-methyl (C.262), tritosulfuron (C.263) (N-[[[4-methoxy-6-(trifluoromethyl)-1,3,5-triazin-2-yl]amino]carbonyl]-2-(trifluoromethyl)-benzenesulfonamide (C.264), known from DE 4 038 430), N-[[[(4,6-dimethoxy-2-pyrimidinyl)amino]carbonyl]-3-(N-methyl-N-methylsulfonylamino])-2-pyridinesulfonamide (C.265), (cf. WO-A-92/10660), N-[[(4,6-dimethoxy-2-pyrimidinyl)amino]carbonyl]-3-(N-methyl-N-methylsulfonylamino)-2-pyridinesulfonamide (C.266), (cf. WO-A-92/10660), 4-(4,5-dihydro-4-methyl-5-oxo-3-trifluoromethyl-1H-1,2,4-triazol-1-yl)-2-(ethylsulfonylamino)-5-fluorobenzenecarbothioamide (C.267, HWH4991, cf. WO-A-95/30661), 2-chloro-N-[1-(2,6-dichloro-4-difluoromethylphenyl)-4-nitro-1H-pyrazol-5-yl]propanecarboxamide (C.268, SLA5599, cf. EP-A-303153), [2-chloro-3-(4,5-dihydro-3-isoxazolyl)-4-methylsulfonylphenyl]-(5-hydrox-1-methyl-1H-pyrazol-4-yl)methanone (C.269) (cf. WO-A-96/26206, WO-A-98/31681), [3-(4,5-dihydro-3-isoxazolyl)-2-methyl-4-methylsulfonylphenyl]-(5-hydrox-1-methyl-1H-pyrazol-4-yl)methanone (C.270) (cf. WO-A-96/26206, WO-A-98/31681), [3-[2-chloro-3[(2,6-dioxocyclohexyl)carbonyl]-6-ethylsulfonylphenyl]-5-isoxazolyl]acetonitrile (C.271) (cf. WO-A-01/28341), 2-[2-chloro-4-methylsulfonyl-3-[(2,2,2-trifluoroethoxy)methyl]benzoyl]-1,3-cyclohexanedione (C.272) (cf. WO-A-01/28341), and 2-[[5,8-dimethyl-1,1-dioxido-4-(2-pyrimidinyloxy)-3,4-dihydro-2H-thiochromen-6-yl]carbonyl]-1,3-cyclohexanedione (C.273) (cf. WO-A-01/28341).

It has now surprisingly been found that the above-defined active ingredient combinations of the substituted thien-3-ylsulfonylamino(thio)carbonyltriazolin(thi)ones of the formula (I) and the above-recited active ingredients of group 2 and where appropriate 3 as well combine very good crop plant tolerance with a particularly high herbicidal activity and can be used in various crops, particularly in cotton, barley, potatoes, corn, oilseed rape, rice, rye, soya, sunflowers, wheat, sugarcane, and sugarbeet, especially in barley, corn, rice, and wheat, for selectively controlling monocotyledonous and dicotyledonous weeds, and that they can also be used for controlling monocotyledonous and dicotyledonous weeds in the semiselective and nonselective segment.

Surprisingly the herbicidal activity of the active ingredient combinations of the invention comprising compounds of the above-listed groups 1 and 2 is considerably higher than the sum of the actions of the individual active ingredients.

Consequently there is an unforeseeable synergistic effect and not merely an additive effect. The novel active ingredient compositions are well tolerated in numerous crops, and also provide effective control of weeds which are otherwise difficult to control. The new active ingredient combinations therefore constitute a valuable enrichment of herbicides.

The synergistic effect of the active ingredient combinations of the invention is particular pronounced at certain concentration ratios. Nevertheless it is possible to vary the weight ratios of the active ingredients in the active ingredient combinations within relatively wide ranges. Generally speaking there are 0.001 to 1000 parts by weight, preferably 0.002 to 500 parts by weight, more preferably 0.01 to 100 parts by weight, and most preferably 0.1 to 50 parts by weight of active ingredient of group 2 per part by weight of active ingredient of the formula (I).

It is to be considered surprising that, from a multiplicity of known safeners or antidotes which are capable of antagonizing the damaging action of a herbicide on the crop plants, it is specifically the above-recited compounds of group 3 that are suitable for eliminating almost completely the damaging effect of active ingredients of the formula (I) and their salts, where appropriate in combination as well with one or more of the above-recited active ingredients of group 2, on the crop plants, and of doing so without at the same time impairing the herbicidal activity toward the weeds.

The advantageous effect of the crop plant tolerance of the active ingredient combinations of the invention is likewise particularly pronounced at certain concentration ratios. Nevertheless it is possible to vary the weight ratios of the active ingredients in the active ingredient combinations within relatively wide ranges. Generally speaking there are 0.001 to 1000 parts by weight, preferably 0.01 to 100 parts by weight, more preferably 0.1 to 25 parts by weight, and most preferably 1 to 10 parts by weight of one of the crop plant tolerance promoter compounds (antidotes/safeners) specified above under (c) per part by weight of active ingredient of the formula (I) or its mixtures with active ingredients of group 2.

In accordance with the invention it is possible to treat all plants and plant parts. By plants here are meant all plants and plant populations, such as desired and unwanted wild plants or crop plants (including naturally occurring crop plants). Crop plants may be plants which can be obtained by conventional breeding and optimization methods or by methods of biotechnology and gene technology, or combinations of these methods, including transgenic plants and including plant cultivars which can or cannot be protected by varietal property rights. By plant parts are meant above-ground and below-ground plant parts and organs of plants, such as the shoot, leaf, flower, and root, examples that may be mentioned being leaves, needles, stems, trunks, flowers, fruit bodies, fruits, and seeds, and also roots, tubers, and rhizomes. The plant parts also include vegetative and generative propagation material, examples being seedlings, tubers, rhizomes, cuttings, and seeds.

The plants and plant parts are treated in accordance with the invention with the active ingredient combinations directly or by causing the combinations to act on their environment, habitat or storage area, in accordance with the typical treatment methods, such as by dipping, spraying, evaporating, fogging, broadcasting, spreading, and, in the case of propagation material, particularly in the case of seeds, additionally by single or multiple coating.

As already mentioned above, it is possible to use the active ingredient combinations of the invention, with or without addition of compounds of group 3, to treat all plants and their parts. In one preferred embodiment wild plant species and plant cultivars or those obtained by conventional biological breeding methods, such as crossing or protoplast fusion, and parts of such plants, are treated. In a further preferred embodiment transgenic plants and plant cultivars obtained by methods of gene technology, where appropriate in combination with conventional methods (genetically modified organisms), and parts of these plants, are treated. The term "parts" or "parts of plants" or "plant parts" has been explained above.

With particular preference plants of the plant cultivars which are in each case commercially customary or in use are treated in accordance with the invention. By plant cultivars are meant plants having defined properties ("traits"), which have been obtained by conventional breeding, by mutagenesis or else by recombinant DNA techniques. These may be cultivars, biotypes, and genotypes.

Depending on the plant species or plant cultivars, their location, and growth conditions (soils, climate, vegetation period, nutrition), the treatment in accordance with the invention may also result in superadditive ("synergistic") effects. Thus, for example, reduced application rates and/or extensions to the spectrum of action and/or a boost in the action of the compounds and compositions which can be used in accordance with the invention, including in combination with other active agrochemical ingredients, better growth of crop plants, increased tolerance of crop plants toward high or low temperatures, increased tolerance of crop plants against drought or against water content or soil salt content, increased flowering performance, easier harvesting, accelerated maturation, higher harvest yields, higher quality and/or higher nutritional value of the harvested products, better storage qualities and/or processability of the harvested products are possible which exceed the effects which were actually anticipated.

The preferred transgenic plants or plant cultivars (i.e., those obtained by gene technology) for inventive treatment include all plants which by virtue of the genetic modification have received genetic material which gives these plants particularly advantageous useful properties ("traits"). Examples of such properties are improved plant growth, increased tolerance to high or low temperatures, increased tolerance to drought or to water content or soil salt content, increased flowering performance, easier harvesting, accelerated maturation, higher harvest yields, higher quality and/or higher nutritional value of the harvested products, better storage qualities and/or processability of the harvested products. Additional and particularly emphasized examples of such properties are a heightened defense by the plants toward animal and microbial pests, such as toward insects, mites, phytopathogenic fungi, bacteria and/or viruses, and increased tolerance of the plants toward certain active herbicidal ingredients. Examples of transgenic plants include the major crop plants, such as cereals (wheat, rice), corn, soya, potatoes, cotton, oilseed rape, and also fruit plants (with the fruits being apples, pears, citrus fruits, and grapes), with particular emphasis being given to corn, soya, potatoes, cotton, and oilseed rape. Properties ("traits") which are particularly emphasized are the increased defense of the plants toward insects as a result of toxins which are formed in the plants, particularly those which are generated in the plants by the genetic material from Bacillus thuringiensis (e.g., by the genes CryIA(a), CryIA(b), CryIA(c), CryIIA, CryIIIA, CryIIIB2, Cry9c Cry2Ab, Cry3Bb, and CryIF, and also combinations thereof) (referred to below as "Bt plants"). Traits that are also particularly emphasized are the heightened defense of plants against fungi, bacteria, and viruses as a result of systemic acquired resistance (SAR), systemin, phytoalexins, elicitors, and also resistance genes, and toxins and proteins expressed correspondingly. Traits that are additionally particularly emphasized are the increased tolerance of the plants toward certain active herbicidal ingredients, examples being imidazolinones, sulfonylureas, glyphosate or phosphinothricin (e.g. "PAT" gene). The genes which impart the desired traits in question may also occur in combinations with one another in the transgenic plants. Examples that may be mentioned of "Bt plants" include corn varieties, cotton varieties, soya varieties, and potato varieties, which are sold under the trade names YIELD GARD® (e.g., corn, cotton, soya), KnockOut® (e.g, corn), StarLink® (e.g., corn), Bollgard® (cotton), Nucotn® (cotton), and NewLeaf® (potatoes). Examples that may be mentioned of herbicide-tolerant plants include corn varieties, cotton varieties, and soya varieties, which are sold under the trade names Roundup Ready® (tolerance to glyphosate e.g, corn, cotton, soya), Liberty Link® (tolerance to phosphinothricin, e.g., oilseed rape), IMI® (tolerance to imidazolinones), and STS® (tolerance to sulfonylureas, e.g, corn). Other herbicide-resistant plants (bred conventionally for herbicide tolerance) that may be mentioned include the varieties (corn, for example) sold under the Clearfield® name. It will be appreciated that these statements also apply to any varieties of plant which are developed in the future or come onto the market in the future and possess these genetic traits or traits to be developed in the future.

The plants listed can be treated with particular advantage with the active ingredient combinations of the invention, such treatment being accompanied not only by the effective control of the weed plants but also by the abovementioned synergistic effects with the transgenic plants or plant cultivars. The ranges of preference indicated above for the active ingredients and/or mixtures also apply for the treatment of these plants.

Particular emphasis may be given to the treatment of plants with the compounds and/or mixtures recited specifically in the present text.

The active ingredient combinations of the invention may be used in connection for example with the following plants:

Dicotyledonous weeds of the following genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thiaspi, Trifolium, Urtica, Veronica, Viola, Xanthium.*

Dicotyledonous crops of the following genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the following genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the following genera: *Allium, Ananas, Asparagus, Avena, Hordeum, Oryza, Panicum, Saccharum, Secale, Sorghum, Triticale, Triticum, Zea.*

The use of the active ingredient combinations of the invention is nevertheless by no means restricted to these genera, but instead extends in the same way to other plants as well.

The active ingredient combinations for use in accordance with the invention may be employed not only in conventional cultivation methods (suitably spaced row crops) in plantation crops (e.g., grapevines, fruit, citrus) and also in industrial plant and rail tracks, on paths and squares, but also for stubble treatment and in the minimum tillage method. They are additionally suitable as desiccants (haulm killing in potatoes, for example) or as defoliants (in cotton, for example). Furthermore, they are suitable for use on non-crop areas. Further fields of use are in nurseries, forest, grassland, and the production of ornamentals.

The active ingredient combinations can be converted into the customary formulations, such as solutions, emulsions, wettable powders, suspensions, powders, dusts, pastes, soluble powders, granules, suspension-emulsion concentrates, natural substances impregnated with active ingredient, and synthetic substances impregnated with active ingredient, and also microencapsulations in polymeric substances.

These formulations are produced in a known way, such as by mixing the active ingredients with extenders, in other words with liquid solvents and/or solid carriers, where appropriate with the use of surface-active agents, in other words emulsifiers and/or dispersants and/or foam-formers.

Where water is used as an extender it is also possible, for example, for organic auxiliary solvents to be used. Suitable liquid solvents include essentially the following: aromatics, such as xylene, toluene, or alkylnaphthalenes, chlorinated aromatics, and chlorinated aliphatic hydrocarbons, such as chlorobenzenes, chloroethylenes or methylene chloride, aliphatic hydrocarbons, such as cyclohexane or paraffins, e.g., petroleum fractions, mineral oils and vegetable oils, alcohols, such as butanol or glycol and also their ethers and esters, ketones such as acetone, methyl ethyl ketone, methyl isobutyl ketone or cyclohexanone, strongly polar solvents, such as dimethylformamide and dimethyl sulfoxide, and also water.

Suitable solid carriers include the following:

e.g., ammonium salts and fine powders of natural minerals, such as kaolins, clays, talc, chalk, quartz, attapulgite, montmorillonite or diatomaceous earth, and fine powders of synthetic minerals, such as highly disperse silica, alumina, and silicates; suitable solid carriers for granules include the following: e.g., crushed and fractionated natural minerals such as calcite, marble, pumice, sepiolite, dolomite, and also synthetic granules of organic and inorganic fine powders, and also granules of organic material such as sawdust, coconut shells, corn cobs and tobacco stems; suitable emulsifiers and/or foam formers include the following: e.g., nonionic and anionic emulsifiers, such as polyoxyethylene-fatty acid esters, polyoxyethylene-fatty alcohol ethers, e.g., alkylaryl polyglycol ethers, alkylsulfonates, alkyl sulfates, arylsulfonates, and protein hydrolysates; suitable dispersants include the following: e.g., lignin-sulfite waste liquors and methylcellulose.

Within the formulations it is possible to use stickers such as carboxymethylcellulose, natural and synthetic polymers in powder, granule or latex form, such as gum Arabic, polyvinyl alcohol, polyvinyl acetate, and also natural phospholipids, such as cephalins and lecithins, and synthetic phospholipids. Further possible additives include mineral and vegetable oils.

It is possible to use dyes and inorganic pigments, examples being iron oxide, titanium oxide, Prussian blue, and organic dyes, such as alizarin dyes, azo dyes, and metal phthalocyanine dyes, and trace nutrients such as salts of iron, manganese, boron, copper, cobalt, molybdenum, and zinc.

The formulations contain in general between 0.1 and 95 percent by weight of active ingredients, preferably between 0.5% and 90%.

The active ingredient combinations of the invention are applied generally in the form of ready-made-up formulations. The active ingredients contained in the active ingredient combinations may alternatively be mixed in individual formulations for application; that is, may be applied in the form of tank mixes.

The new active ingredient combinations may find use as such or in their formulations additionally in a mixture with other known herbicides as well, in which case, again, ready-made-up formulations or tank mixes are a possibility. Also possible is a mixture with other known active ingredients, such as fungicides, insecticides, acaricides, nematicides, bird repellents, growth substances, plant nutrients, and soil conditioners. For certain end uses, particularly in post emergence application, it may additionally be advantageous to incorporate into the formulations, as further additives, plant-compatible mineral or vegetable oils (an example being the commercial product "Rako Binol") or ammonium salts, such as ammonium sulfate or ammonium thiocyanate, for example.

The new active ingredient combinations can be employed as they are, in the form of their formulations or of the use forms prepared from them by further dilution, such as ready-to-use solutions, suspensions, emulsions, powders, pastes, and granules. They are applied in conventional fashion, such as by pouring, spraying, atomizing, dusting or broadcasting.

The active ingredient combinations of the invention can be applied before and after the emergence of the plants, in other words pre-emergence and post emergence. They can also be incorporated into the soil before sowing.

The good herbicidal action of the new active ingredient combinations is apparent from the examples below. Whereas the individual active ingredients exhibit weaknesses in their herbicidal action, the combinations all show a very good weed action which goes beyond a simple summation of action.

A synergistic effect is present in the case of herbicides whenever the herbicidal action of the active ingredient combination is greater than that of the individual active ingredients applied.

The anticipated action for a given combination of two herbicides can be calculated as follows (cf. COLBY, S. R.: "Calculating synergistic and antagonistic responses of herbicide combinations", Weeds 15, pages 20-22, 1967):

If $X$=% damage by herbicide A (active ingredient of formula I) at p kg/ha application rate and $Y$=% damage by herbicide B (active ingredient of Formula II) at q kg/ha application rate and $E$=the expected damage of the herbicides A and B at p and q kg/ha application rate, then $$E = X + Y - (X*Y/100).$$

If the actual damage is greater than calculated, then the combination is superadditive in its effect; in other words, it shows a synergistic effect.

The anticipated action for a given combination of three herbicides may likewise be taken from the literature cited above.

TABLE A-1

| Active ingredient or active ingredient combination | Application rate(s) (g a.i./ha) | Action against *Alopecurus myosuroides* (%) | Calculated action by Colby (%) |
|---|---|---|---|
| Compound (I-2) | 1.88 | 45 | |
| Compound (B.7) | 3.75 | 0 | |
| Compound (I-2) + Compound (B.7) | 1.88 + 3.75 | 53 | 45 |

TABLE A-2

| Active ingredient or active ingredient combination | Application rate(s) (g a.i./ha) | Action against *Amaranthus rudis* (%) | Calculated action by Colby (%) |
|---|---|---|---|
| Compound (I-2) | 1.88 | 20 | |
| Compound (B.7) | 3.75 | 35 | |
| Compound (I-2) + Compound (B.7) | 1.88 + 3.75 | 50 | 48 |

TABLE A-3

| Active ingredient or active ingredient combination | Application rate(s) (g a.i./ha) | Action against *Galium aparine* (%) | Calculated action by Colby (%) |
|---|---|---|---|
| Compound (I-2) | 1.88 | 73 | |
| Compound (B.7) | 3.75 | 0 | |
| Compound (I-2) + Compound (B.7) | 1.88 + 3.75 | 80 | 73 |

TABLE A-3

| Active ingredient or active ingredient combination | Application rate(s) (g a.i./ha) | Action against *Alopecurus myosuroides* (%) | Calculated action by Colby (%) |
|---|---|---|---|
| Compound (I-2) | 1.88 | 45 | |
| Compound (B.7) | 7.5 | 0 | |
| Compound (I-2) + Compound (B.7) | 1.88 + 7.5 | 53 | 45 |

TABLE A-4

| Active ingredient or active ingredient combination | Application rate(s) (g a.i./ha) | Action against *Amaranthus rudis* (%) | Calculated action by Colby (%) |
|---|---|---|---|
| Compound (I-2) | 1.88 | 20 | |
| Compound (B.7) | 7.5 | 0 | |
| Compound (I-2) + Compound (B.7) | 1.88 + 7.5 | 45 | 20 |

TABLE A-5

| Active ingredient or active ingredient combination | Application rate(s) (g a.i./ha) | Action against *Alopecurus myosuroides* (%) | Calculated action by Colby (%) |
|---|---|---|---|
| Compound (I-2) | 1.88 | 45 | |
| Compound (B.3) | 3.75 | 0 | |
| Compound (I-2) + Compound (B.3) | 1.88 + 3.75 | 58 | 45 |

TABLE A-6

| Active ingredient or active ingredient combination | Application rate(s) (g a.i./ha) | Action against *Avena fatua* (%) | Calculated action by Colby (%) |
|---|---|---|---|
| Compound (I-2) | 1.88 | 83 | |
| Compound (B.3) | 3.75 | 0 | |
| Compound (I-2) + Compound (B.3) | 1.88 + 3.75 | 90 | 83 |

TABLE A-7

| Active ingredient or active ingredient combination | Application rate(s) (g a.i./ha) | Action against *Avena fatua* (%) | Calculated action by Colby (%) |
|---|---|---|---|
| Compound (I-2) | 1.88 | 20 | |
| Compound (B.3) | 3.75 | 88 | |
| Compound (I-2) + Compound (B.3) | 1.88 + 3.75 | 93 | 90 |

TABLE A-8

| Active ingredient or active ingredient combination | Application rate(s) (g a.i./ha) | Action against *Alopecurus myosuroides* (%) | Calculated action by Colby (%) |
|---|---|---|---|
| Compound (I-2) | 1.88 | 45 | |
| Compound (B.2) | 6.25 | 10 | |
| Compound (I-2) + Compound (B.2) | 1.88 + 6.25 | 55 | 45 |

TABLE A-9

| Active ingredient or active ingredient combination | Application rate(s) (g a.i./ha) | Action against *Avena fatua* (%) | Calculated action by Colby (%) |
|---|---|---|---|
| Compound (I-2) | 1.88 | 82 | |
| Compound (B.2) | 6.25 | 0 | |
| Compound (I-2) + Compound (B.2) | 1.88 + 6.25 | 85 | 82 |

TABLE A-9

| Active ingredient or active ingredient combination | Application rate(s) (g a.i./ha) | Action against Amaranthus rudis (%) | Calculated action by Colby (%) |
|---|---|---|---|
| Compound (I-2) | 1.88 | 20 | |
| Compound (B.2) | 6.25 | 94 | |
| Compound (I-2) + Compound (B.2) | 1.88 + 6.25 | 97 | 95 |

The invention claimed is:

1. A composition comprising an effective amount of an active ingredient combination comprising
   (a) at least one substituted thien-3-ylsulfonylamino(thio)carbonyl-triazolin(thi)one of the formula (I)

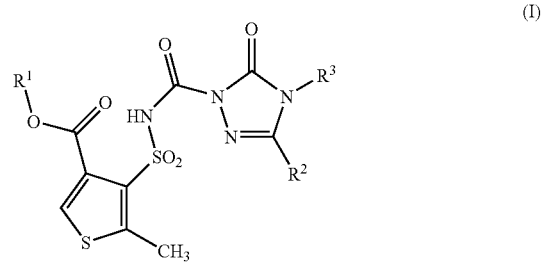

in which $R^1$ is optionally cyano-, halogen- or $C_1$-$C_4$-alkoxy-substituted alkyl having 1 to 6 carbon atoms, $R^2$ is hydrogen, hydroxyl, mercapto, amino, cyano, fluorine, chlorine, bromine or iodine, is optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, is in each case optionally fluorine-, chlorine- and/or bromine-substituted alkenyl or alkynyl having in each case 2 to 6 carbon atoms, is in each case optionally fluorine-, chlorine-, cyano-, $C_1$-$C_4$-alkoxy- or $C_1$-$C_4$-alkoxy-carbonyl-substituted alkoxy, alkylthio, alkylamino or alkylcarbonylamino having in each case 1 to 6 carbon atoms in the alkyl group, is alkenyloxy, alkynyloxy, alkenylthio, alkynylthio, alkenylamino or alkynylamino having in each case 3 to 6 carbon atoms in the alkenyl or alkynyl group, is dialkylamino having in each case 1 to 4 carbon atoms in the alkyl groups, is in each case optionally methyl- and/or ethyl-substituted aziridino, pyrrolidino, piperidino or morpholino, is in each case optionally fluorine-, chlorine-, bromine-, cyano- and/or $C_1$-$C_4$-alkyl-substituted cycloalkyl, cycloalkenyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl or cycloalkenyl group and optionally 1 to 4 carbon atoms in the alkyl moiety, or is in each case optionally fluorine-, chlorine-, bromine-, cyano-, nitro-, $C_1$-$C_4$-alkyl-, trifluoromethyl-, $C_1$-$C_4$-alkoxy- and/or $C_1$-$C_4$-alkoxy-carbonyl-substituted aryl, arylalkyl, aryloxy, arylalkoxy, arylthio, arylalkylthio, arylamino or arylalkylamino having in each case 6 or 10 carbon atoms in the aryl group and optionally 1 to 4 carbon atoms in the alkyl moiety, $R^3$ is hydrogen, hydroxyl, amino, cyano, is $C_2$-$C_{10}$-alkylideneamino, is optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, is in each case optionally fluorine-, chlorine- and/or bromine-substituted alkenyl or alkynyl having in each case 2 to 6 carbon atoms, is in each case optionally fluorine-, chlorine-, bromine-, cyano-, $C_1$-$C_4$-alkoxy- or $C_1$-$C_4$-alkoxy-carbonyl-substituted alkoxy, alkylamino or alkyl-carbonylamino having in each case 1 to 6 carbon atoms in the alkyl group, is alkenyloxy having 3 to 6 carbon atoms, is dialkylamino having in each case 1 to 4 carbon atoms in the alkyl groups, is in each case optionally fluorine-, chlorine-, bromine-, cyano- and/or $C_1$-$C_4$-alkyl-substituted cycloalkyl, cycloalkylamino or cycloalkylalkyl having in each case 3 to 6 carbon atoms in the alkyl group and optionally 1 to 4 carbon atoms in the alkyl moiety, or is in each case optionally fluorine-, chlorine-, bromine-, cyano-, nitro-, $C_1$-$C_4$-alkyl-, trifluoromethyl- and/or $C_1$-$C_4$-alkoxy-substituted aryl or arylalkyl having in each case 6 or 10 carbon atoms in the aryl group and optionally 1 to 4 carbon atoms in the alkyl moiety or salts of the compounds of the formula (I)

and (b)

(Compound B.3)

wherein there are 0.1 to 50 parts by weight of Compound B-3 per part by weight of the at least one substituted thien-3-ylsulfonylamino(thio)carbonyl-triazolin(thi)one of the formula (I) and, if desired, additionally (c) a crop plant tolerance promoter compound from the following group of compounds:

4-dichloroacetyl-1-oxa-4-azaspiro[4.5]decane (AD-67), 4-dichloroacetyl-3,4-dihydro-3-methyl-2H-1,4-benzoxazine (benoxacor), 5-chloroquinoxalin-8-oxyacetic acid 1-methylhexyl ester (cloquintocet-mexyl), 2,4-dichlorophenoxyacetic acid (2,4-D), 2,2-dichloro-N,N-di-2-propenylacetamide (dichlormid), N-(4-methylphenyl)-N'-(1-methyl-1-phenylethyl)urea (daimuron), 4,6-dichloro-2-phenylpyrimidine (fenclorim), 1-(2,4-dichlorophenyl)-5-trichloromethyl-1H-1,2,4-triazole-3-carboxylic acid ethyl ester (fenchlorazole-ethyl), 2-chloro-4-trifluoromethylthiazole-5-carboxylic acid phenylmethyl ester (flurazole), 4-chloro-N-(1,3-dioxolan-2-ylmethoxy)-α-trifluorophenone oxime (fluxofenim), 3-dichloroacetyl-5-(2-furanyl)-2,2-dimethyloxazolidine (furilazole), ethyl 4,5-dihydro-5,5-diphenyl-3-isoxazolecarboxylate (isoxadifen-ethyl), (4-chloro-2-methylphenoxy)acetic acid (MCPA), (+-)-2-(4-chloro-2-methylphenoxy)propanoic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191, CAS Reg. No. 96420-72-3), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2,5-trimethyloxazolidine (R-29148), N-cyclopropyl-4-[[(2-methoxy-5-methylbenzoyl)amino]sulfonyl]benzamide, N-[[(4-methylaminocarbonylamino)phenyl]-sulfonyl-2-methoxybenzamide, and compounds of the formula (II) below, (II)

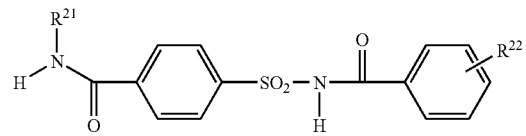

in which
$R^{21}$ and $R^{22}$ are as defined in the following table:

| $R^{21}$ | $R^{22}$ |
|---|---|
| cyclopropyl | 2-OCH$_3$ |
| cyclopropyl | 2-OCH$_3$, 5-Cl |
| ethyl | 2-OCH$_3$ |
| isopropyl | 2-OCH$_3$, 5-Cl |
| isopropyl | 2-OCH$_3$. |

2. The composition as claimed in claim 1, wherein the crop plant tolerance promoter compound is selected from the active ingredients benoxacor, mefenpyr-diethyl, fenchlorazole-ethyl, isoxadifen-ethyl, cloquintocet-mexyl, and the compound N-cyclopropyl-4-[[[(2-methoxybenzoyl)amino]sulfonyl]benzamide.

3. A method of controlling weeds, comprising applying the composition of claim 1 to weeds and/or their habitat, wherein said composition further comprises surface active agents and/or extenders.

4. A process for producing a herbicidal composition comprising, mixing a composition of claim 1 with surface-active agents and/or extenders.

5. A composition according to claim 1, wherein $R^1$ is CH$_3$; $R^2$ is —OCH$_3$; and $R^3$ is CH$_3$.

* * * * *